(12) United States Patent
Uehara et al.

(10) Patent No.: US 10,174,281 B2
(45) Date of Patent: Jan. 8, 2019

(54) BIOMASS TREATMENT SYSTEM

(71) Applicant: MITSUBISHI HITACHI POWER SYSTEMS ENVIRONMENTAL SOLUTIONS, LTD., Yokohama-shi, Kanagawa (JP)

(72) Inventors: Ryosuke Uehara, Kobe (JP); Seiji Kobayashi, Kobe (JP); Minoru Genta, Kobe (JP); Seiichi Terakura, Kobe (JP)

(73) Assignee: MITSUBISHI HITACHI POWER SYSTEMS ENVIRONMENTAL SOLUTIONS, LTD., Kanagawa (JP)

( * ) Notice: Subject to any disclaimer, the term of this patent is extended or adjusted under 35 U.S.C. 154(b) by 0 days.

(21) Appl. No.: 14/767,576

(22) PCT Filed: Feb. 28, 2013

(86) PCT No.: PCT/JP2013/055500
§ 371 (c)(1),
(2) Date: Aug. 12, 2015

(87) PCT Pub. No.: WO2014/132409
PCT Pub. Date: Sep. 4, 2014

(65) Prior Publication Data
US 2016/0010051 A1    Jan. 14, 2016

(51) Int. Cl.
C12M 1/00 (2006.01)
C12P 19/02 (2006.01)
(Continued)

(52) U.S. Cl.
CPC ............ *C12M 45/20* (2013.01); *C08B 15/00* (2013.01); *C08H 6/00* (2013.01); *C08H 8/00* (2013.01);
(Continued)

(58) Field of Classification Search
CPC ...... C12M 33/22; C12M 45/04; C12M 45/20; C12M 45/06; C12M 21/12; C12M 33/16;
(Continued)

(56) References Cited
U.S. PATENT DOCUMENTS 4,370,172 A * 1/1983 Gueissaz .................. B01J 3/02
127/1
8,328,947 B2 * 12/2012 Anand et al. ............ C08H 8/00
127/1
(Continued)

FOREIGN PATENT DOCUMENTS

JP    41-11125 U    5/1966
JP    57-55514 U    4/1982
(Continued)

OTHER PUBLICATIONS

International Search Report and Written opinion dated Apr. 2, 2013 in International Application No. PCT/JP2013/055500.
(Continued)

*Primary Examiner* — Gautam Prakash
(74) *Attorney, Agent, or Firm* — Hauptman Ham, LLP

(57) ABSTRACT

This biomass treatment system includes: a hydrothermal decomposition section for decomposing the cellulose, hemicellulose and lignin contained in a biomass as a raw material under high-temperature and high-pressure conditions in a main section, namely a tank having a gas-liquid interface, and thus removing a lignin component and a hemicellulose component from the biomass; a discharge section for discharging a biomass solid (a component insoluble in hot-water) obtained by the decomposition; a slurrying tank which is connected to the discharge section and in which the discharged biomass solid is slurried in water fed thereinto to form a biomass slurry; and a solid-liquid separation apparatus including both a settling tank which is provided on a discharge line for discharging the biomass slurry and in
(Continued)

which the biomass slurry is settled and a scooping-up and conveying means for scooping up the biomass solid deposited at the bottom of the settling tank and separating the solid biomass component from water.

4 Claims, 6 Drawing Sheets

(51) Int. Cl.
| | |
|---|---|
| *C12P 19/14* | (2006.01) |
| *C12P 7/02* | (2006.01) |
| *C08H 8/00* | (2010.01) |
| *C13K 1/02* | (2006.01) |
| *C12P 7/10* | (2006.01) |
| *C08B 15/00* | (2006.01) |
| *C08H 7/00* | (2011.01) |
| *C12M 1/26* | (2006.01) |
| *C12M 1/33* | (2006.01) |

(52) U.S. Cl.
CPC ............ *C12M 21/12* (2013.01); *C12M 33/16* (2013.01); *C12M 45/02* (2013.01); *C12M 45/04* (2013.01); *C12M 45/06* (2013.01); *C12P 7/02* (2013.01); *C12P 7/10* (2013.01); *C12P 19/02* (2013.01); *C12P 19/14* (2013.01); *C13K 1/02* (2013.01); *C12M 33/22* (2013.01); *C12P 2201/00* (2013.01); *C12P 2203/00* (2013.01); *Y02E 50/16* (2013.01); *Y02T 50/678* (2013.01)

(58) Field of Classification Search
CPC ... C08H 6/00; C08H 8/00; C12P 19/02; C12P 19/14; C12P 7/10; C12P 7/02; C12P 2203/00; C12P 2201/00; C13K 1/02; C08B 15/00; Y02E 50/16
See application file for complete search history.

(56) References Cited

U.S. PATENT DOCUMENTS

| | | | |
|---|---|---|---|
| 2012/0009626 A1 | 1/2012 | Suzuki et al. | |
| 2012/0279495 A1* | 11/2012 | Kitano et al. | ............ B01F 7/18 127/1 |

FOREIGN PATENT DOCUMENTS

| | | |
|---|---|---|
| JP | 58-55012 A | 4/1983 |
| JP | 4-293504 A | 10/1992 |
| JP | 6-158370 A | 6/1994 |
| JP | 8-71309 A | 3/1996 |
| JP | 9-507386 A | 7/1997 |
| JP | 11-506934 A | 6/1999 |
| JP | 2001-170698 A | 6/2001 |
| JP | 2001-219007 A | 8/2001 |
| JP | 2005-168335 A | 6/2005 |
| JP | 2009-183154 A | 8/2009 |
| JP | 2009-183805 A | 8/2009 |
| JP | 4764527 B1 | 9/2011 |
| WO | 95/17517 A1 | 6/1995 |
| WO | 96/40970 A1 | 12/1996 |
| WO | 20121004895 A1 | 1/2012 |

OTHER PUBLICATIONS

Written Opinion dated Apr. 2, 2013, corresponding to International application No. PCT/JP2013/055500.
Office Action in JP Application No. 2015-502670, dated Dec. 22, 2015.
Office Action in AU Application No. 2013380113, dated Jan. 8, 2016.
Office Action in JP Application No. 2015-502670, dated May 24, 2016.
Notice of Acceptance in AU Application No. 2013380113, dated Jul. 8, 2016.
Office Action in JP Application No. 2016-164187, dated Jul. 25, 2017, 7pp.

* cited by examiner

US 10,174,281 B2

BIOMASS TREATMENT SYSTEM

RELATED APPLICATIONS

The present application is a National Phase entry of International Application No. PCT/JP2013/055500, filed Feb. 28, 2013.

TECHNICAL FIELD

The present invention relates to a biomass treatment system capable of efficiently decomposing biomass raw materials, a saccharide solution producing method and an alcohol producing method using biomass raw materials, and a method for producing saccharide-derived organic raw materials.

BACKGROUND ART

In conventionally employed techniques for producing ethanol or the like, after saccharification of biomass such as wood or the like by dilute sulfuric acid and concentrated sulfuric acid, solid-liquid separation is performed, and the liquid phase is neutralized and used as a raw material of ethanol fermentation or the like (Patent Document 1, Patent Document 2).

Furthermore, production of raw materials for the chemical industry (for example, lactic fermentation and the like) using saccharides as a starting material is also considered.

Here, biomass refers to accumulation of organisms or organic matter derived from organisms that are incorporated in the substance circulation system of the global biosphere (see JIS K 3600 1258).

Here, sugarcane, corn, and the like currently used as raw materials of alcohols are those originally used for foods, but using these food resources as long-term, stable industrial resources is not desirable from the perspective of an effective foodstuff lifecycle.

For this reason, an important problem is the effective utilization of cellulose resources like herbaceous biomass and wood biomass, which are thought to be useful resources for the future.

In cellulose resources, cellulose content varies from 38 to 50%, hemicellulose component varies from 23 to 32%, and lignin components, which do not serve as fermentation raw materials, also varies from 15 to 22%. Since a study for industrialization has posed numerous problems, in a current state, raw materials are presumed to be fixed and a technology of production system that takes into consideration the versatility of raw materials is not disclosed.

Additionally, in the methods that are more disadvantageous for fermentation raw materials than for starch raw materials to begin with, there is little significance in a production system that considers raw materials to be fixed, considering objectives such as waste problems and global warming prevention measures. The methods need to be widely applicable to general waste. In the current state, the efficiency of enzymatic saccharification itself is poor, which is considered to be a problem for the future. The saccharification rate by acid treatment is also low, around 75% (based on saccharifiable components), due to excessive decomposition of saccharides due to overreaction and the like. Therefore, the ethanol production yield from cellulose-based resources is about 25% (Patent Document 3).

Furthermore, in the conventional art of Patent Documents 1 to 3, a phenomenon has been occurred in which secondary reaction products causes inhibition of enzymatic saccharification and saccharide yield declines. Therefore, hydrothermal decomposition apparatuses that remove enzymatic saccharification-inhibitor substances and increase enzymatic saccharification capability by the cellulose main constituent have been proposed (Patent Documents 4 to 6).

CITATION LIST

Patent Literature

Patent Document 1: Japanese Unexamined Patent Application Publication (Translation of PCT Application) No. H9-507386A
Patent Document 2: Japanese Unexamined Patent Application Publication (Translation of PCT Application) No. H11-506934A
Patent Document 3: Japanese Unexamined Patent Application Publication No. 2005-168335A
Patent Document 4: Japanese Unexamined Patent Application Publication No. 2009-183805A
Patent Document 5: Japanese Unexamined Patent Application Publication No. 2009-183154A
Patent Document 6: Japanese Patent No. 4764527B

SUMMARY OF INVENTION

Technical Problem

Incidentally, in the hydrothermal decomposition apparatus proposed in Patent Document 6, biomass is decomposed by the hydrothermal decomposition apparatus, and then the biomass solid is introduced into a slurry tank where the discharged biomass solid is slurried, but it requires a large amount of water, and separation and concentration of water by a water content separation means are required for saccharifying fermentation of the slurried water.

Thus, the introduction of this water content separation means makes the method more complex and increases the initial cost, and additionally, operating costs rise due to operation of the water content separation means. Therefore, from an economic viewpoint, a simpler method for separating water contents has been sought.

In consideration of the above problems, an object of the present invention is to provide a biomass treatment system having a solid-liquid separation apparatus designed for water reuse that can easily separate the water content from a biomass slurry, a saccharide solution producing method and an alcohol producing method, and an organic raw material producing method that use biomass raw material.

Solution to Problem

A first invention of the present invention for solving the above problems is a biomass treatment system comprising: a biomass treatment section for, by a treatment column having a gas-liquid interface, decomposing a biomass raw material containing cellulose, hemicellulose, and lignin under high-temperature and high-pressure conditions, and thus removing a lignin component and a hemicellulose component from the biomass; a biomass solid discharge section for discharging a biomass solid treated by the biomass treatment section; a slurrying tank connected to the biomass solid discharge section, into which water is poured and the discharged biomass solid is slurried; and a solid-liquid separation apparatus including a settling tank for settling the biomass slurry, the settling tank being provided downstream of the slurrying tank, and a scooping-up and conveying means for separating water while scooping up the biomass solid settled on a bottom of the settling tank.

A second invention is the biomass treatment system according to the first invention, further comprising a saccharification tank for saccharifying the biomass solid separated by the solid-liquid separation apparatus.

A third invention is the biomass treatment system according to the first or second invention, wherein the scooping-up and conveying means is a screw conveyor or a belt conveyor.

A fourth invention is the invention according to any one of the first to third inventions, wherein the biomass treatment section is any one of a hydrothermal decomposition section, an alkali decomposition section, or an acid decomposition section.

A fifth invention is a method of producing a saccharide solution using biomass raw material, the method comprising the steps of: supplying a biomass raw material containing cellulose, hemicellulose, and lignin from atmospheric pressure to increased pressure; decomposing the biomass raw material under high-temperature and high-pressure conditions by a biomass treatment section; and putting a biomass solid discharged from the biomass treatment section is put in a slurrying tank into which water is poured and which is connected to the biomass treatment section, and forming into a biomass slurry; settling the biomass slurry in a settling tank; removing water while scooping up the settled biomass solid by a scooping-up and a conveying means, and enzymatically saccharifying the biomass solid from which water has been removed to produce a saccharide solution.

A sixth invention is a method of producing alcohol, comprising a step of fermenting alcohol using a saccharide solution obtained by the method of producing a saccharide solution using a biomass raw material descried in the fifth invention and producing alcohol.

A seventh invention is a method of producing an organic raw material using a biomass raw material, the method comprising the step of producing any one of alcohols, petroleum oil substitutes, or amino acids by fermentation using a saccharide solution obtained by the method of producing a saccharide solution using a biomass raw material described in the fifth invention.

Advantageous Effects of Invention

According to the present invention, a biomass slurry is settled in a settling tank, and the settled biomass solid undergoes solid-liquid separation by a scooping-up and conveying means, for example, a screw conveyor, thereby removing water and making it into a concentrated biomass slurry. Furthermore, the present invention exhibits the effect of being able to remove water as well as reduce the content of reaction-inhibitor substances when the biomass slurry contains reaction-inhibitor substances.

DESCRIPTION OF EMBODIMENTS

The present invention will be described in detail below in reference to the drawings. Note that the present invention is not limited by these embodiments. Additionally, the constituent elements in the embodiments below include those that can be recognized by persons skilled in the art or those that are substantially the same. Furthermore, in the embodiments, the present invention is described using a hydrothermal decomposition apparatus as a biomass treatment section for treating biomass raw materials, but the present invention is not limited thereto, and the similar operations could be applied in a system that decomposes biomass raw materials by the addition of an acid or alkali.

Embodiment 1

The biomass treatment system according to the present invention will be described in reference to the drawings.

Figure 1:
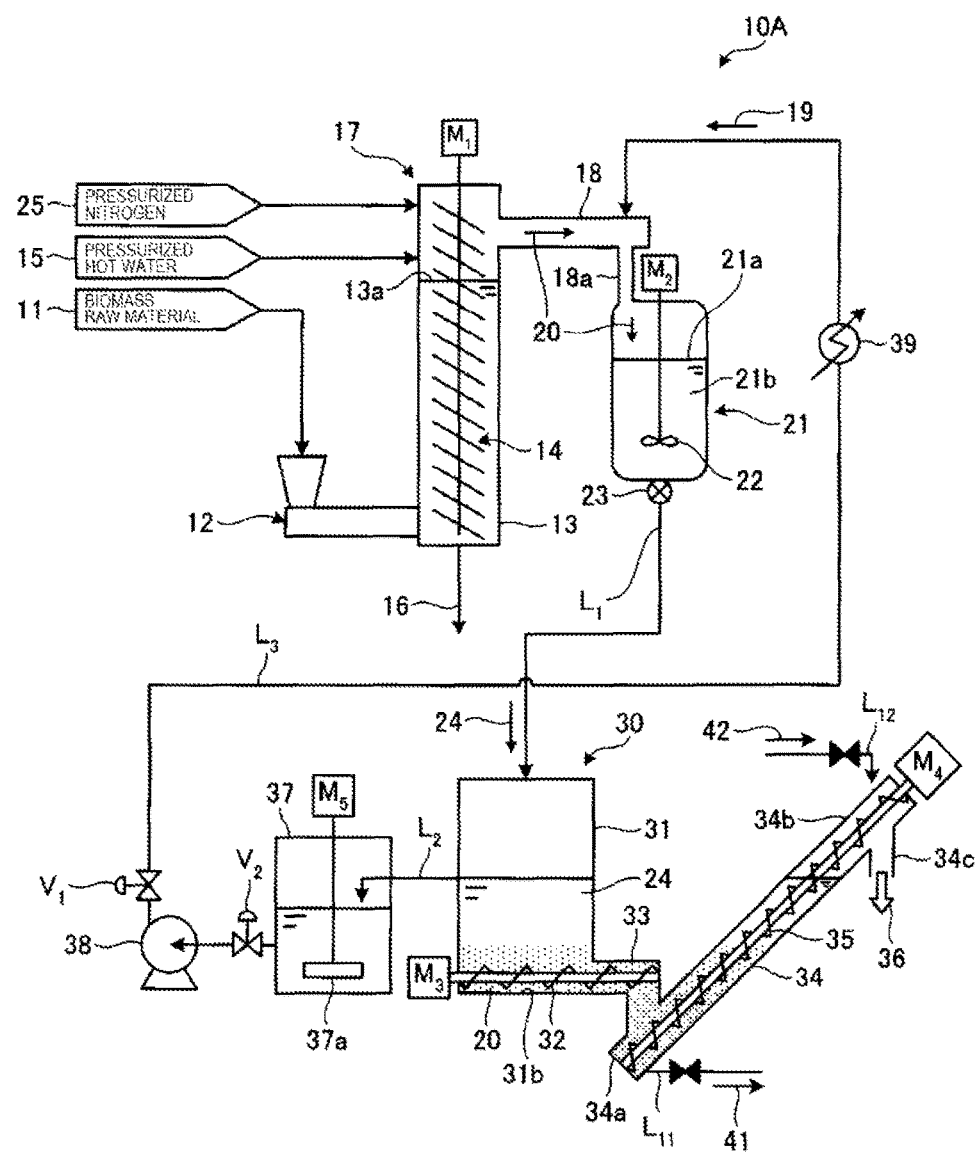
FIG. 1 is a schematic view illustrating a biomass treatment system according to embodiment 1.
Figure 2:
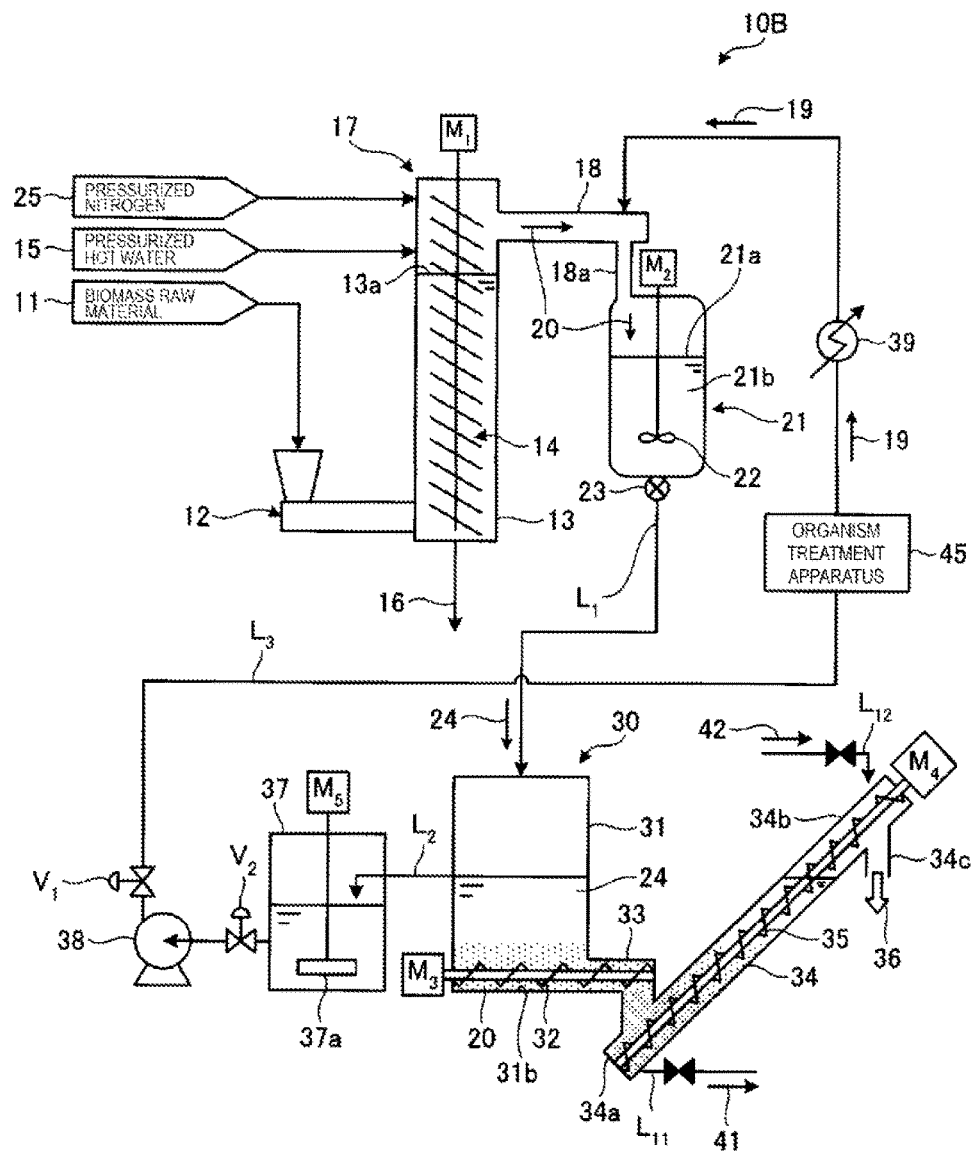
FIG. 2 is a schematic view illustrating another biomass treatment system according to embodiment 1.

FIG. 1 is a schematic view illustrating a biomass treatment system according to embodiment 1. FIG. 2 is a schematic view illustrating another biomass treatment system according to this embodiment.

As illustrated in FIG. 1, a biomass treatment system 10A according to this embodiment has: a hydrothermal decomposition section 17, which is a biomass treatment section for decomposing the cellulose, hemicellulose and lignin contained in a biomass 11 as a raw material under high-temperature and high-pressure conditions in a main section 13, namely a treatment column having a gas-liquid interface 13a, and thus removing a lignin component and a hemicellulose component from the biomass 11; a discharge section 18 for discharging a biomass solid (a component insoluble in hot water) 20 treated by the hydrothermal decomposition section 17; a slurrying tank 21 which is connected to the discharge section 18 and into which the discharged biomass solid 20 is put and water 19 is poured to form a biomass slurry 24; a discharge section 23 for discharging the biomass slurry 24 from increased pressure to atmospheric pressure; and a solid-liquid separation apparatus 30 which includes both a settling tank 31 provided on a discharge line $L_1$ of the biomass slurry 24 discharged from the slurrying tank 21, and in which the biomass slurry 24 is settled, and a scooping-up and conveying section 34 for separating water while scooping up the biomass solid 20 settled on the bottom 31b of the settling tank 31.

In the solid-liquid separation apparatus 30, the biomass slurry 24 is settled in the settling tank 31, and this settled biomass solid 20 undergoes solid-liquid separation by the scooping-up and conveying section 34 such as, for example, a screw conveyor 35, thereby removing water 19 which contains reaction-inhibitor substances, to form a concentrated biomass slurry 36. By removing water 19 in the solid-liquid separation apparatus 30, the solid concentration can be increased. In other words, the biomass solid concentration can be increased up to the water-holding capacity of the biomass solid. As a result, the substrate concentration of a saccharification reaction downstream can be adjusted.

That is, according to this embodiment, by separating water 19 which contains reaction-inhibitor substances from the biomass slurry 24 in the solid-liquid separation apparatus 30, it is possible to efficiently remove the reaction-inhibitor substances, and the reactions downstream become well.

Furthermore, by returning the separated water 19 to the slurrying tank 21 and reusing it, another supply of water required for slurrying can be omitted, and the amount of water used in the plant as a whole can be reduced.

Here, the hydrothermal decomposition section 17 has a biomass supply section 12 for supplying the biomass raw material 11 having cellulose, hemicellulose, and lignin from atmospheric pressure to increased pressure.

Also, in the hydrothermal decomposition section 17, the supplied biomass raw material 11 is conveyed from bottom to top inside the main section 13 by a first screw means 14, which is a conveying means, and pressurized hot water (also referred to as "hot water" hereinafter) 15 is supplied to the interior of the main section 13 from above, which differs from the supply location of the biomass raw material 11. The biomass raw material 11 and the pressurized hot water 15 undergo hydrothermal decomposition while being put in opposing contact, and the hydrothermally decomposed components (lignin component and hemicellulose component) transfer into hot water discharged liquid 16, which consists of pressurized hot water to be discharged, and the lignin component and hemicellulose component are separated from the biomass raw material 11.

Here, a screw means is given as an example of the conveying means in this embodiment, but the conveying means is not limited to a screw means provided that it can convey the biomass solid from bottom to top.

The water 19 put into the slurrying tank 21 may be any provided that it is in the liquid state under pressure in the system in order to form a liquid seal for the purpose of preventing leakage of pressurized nitrogen 25 used for pressurizing. To suppress excessive decomposition of hemicellulose (hemicellulose decomposition initiation temperature: approximately 140° C. to 180° C.) contained in the water content contained in the biomass solid 20, the temperature of the water 19 poured in may be set as appropriate according to the volume of the slurrying tank 21 and the temperature of the biomass solid 20 so as to cool the temperature in the slurrying tank 21 to not greater than 140° C., and more preferably not greater than 100° C. Preferably, the temperature of the water 19 may be appropriately set such that the slurry temperature is not greater than 100° C., so that a stable slurry can be discharged in the discharge section 23 without vaporizing.

Furthermore, the water 19 can be in the range of, for example, from 0° C. to 60° C., and can be reused by circulating the water within the system as will be described later.

Here, in FIG. 1, reference numeral 18a is a passage connecting the biomass solid discharge section 18 and the slurrying tank 21; 22 is a stirring means which stirs inside the slurrying tank 21; 13a is a gas-liquid interface of the main section 13; 21a is a gas-liquid interface of the slurrying tank 21; $L_1$ is a discharge line; $M_1$ is a motor that drives the first screw means 14; and $M_2$ is a motor that drives the stirring means 22.

The biomass (cellulose-based raw material) raw material 11 contains hemicellulose and lignin in addition to cellulose, and specifically, it has a structure in which hemicellulose bundles cellulose, and lignin adheres.

After hydrothermal decomposition, the biomass is divided into a component insoluble in hot water (solid) and a component soluble in hot water. The component insoluble in hot water is primarily cellulose (raw material of C6 saccharide), and the component soluble in hot water is primarily hemicellulose (raw material of C5 saccharide), and saccharides can be obtained by saccharification using individual enzymes.

Thus, the biomass raw material 11 is hydrothermally decomposed in a high-temperature region (from 180° C. to 240° C.) by pressurized hot water 15, and on the hot water side, hemicellulose is dissolved and lignin is decomposed and dissolved, and as a result, hemicellulose and the like are dissolved on the hot water side.

In the state of hot water-solubilized hemicellulose after solubilization in hot water, excessive decomposition occurs in the high-temperature region (from 180° C. to 240° C.).

Because this excessive decomposition of hemicellulose causes a decrease in yield of hemicellulose, which is a raw material of C5 saccharide, excessive decomposition of hot water-solubilized hemicellulose needs to be suppressed.

Furthermore, because mixing of excessively decomposed matter in the hot water is a cause of reaction inhibition in the saccharification step by enzymes and the fermentation steps such as alcohol fermentation in equipment downstream, generation of these inhibitor substances needs to be prevented.

In FIG. 1, a second screw means (not illustrated) is provided in the biomass solid discharge section 18, wherein the second screw means discharges the biomass solid 20, which is insoluble in hot water and has been conveyed from bottom to top by the first screw means 14, to the slurrying tank 21 side. Then, the discharged biomass solid 20 is sequentially dropped from the passage 18a into liquid 21b and slurried by stirring by the stirring means 22 provided in the slurrying tank 21.

Furthermore, water 19 may be supplied from a biomass outlet top section of the biomass solid discharge section 18 such that the biomass solid 20 bridges the passage 18a and does not block it. Additionally, the biomass solid discharge section 18 may be configured, as simply an inclined pipe, to drop the biomass solid 20 by gravity, or such that it discharges the biomass solid 20 into the slurrying tank 21 while being washed out by the water 19 supplied from the top section of the biomass solid discharge section 18.

Furthermore, the biomass solid 20 that was dropped into the liquid 21b in the slurrying tank 21 is cooled by direct heat exchange with the water 19, and as a result, excessive decomposition of the residual hemicellulose, residual lignin, and primary component cellulose by hot water that accompanies the biomass solid 20 is suppressed.

Here, in the gas atmosphere on the top side of the gas-liquid interface 13a of the hydrothermal decomposition section 17, the biomass solid 20 is exposed above the hot water surface (gas-liquid interface 13a) by the first screw means 14. However, due to the presence of the pressurized hot water 15 that accompanies the biomass solid 20, the reaction still proceeds under high-temperature high-pressure conditions, and thus the reaction can be quenched by putting the biomass solid 20 into the liquid 21b in the slurrying tank 21.

Thus, by quenching the reaction, excessive decomposition of the residual hemicellulose, residual lignin, and primary component cellulose is suppressed, excessive decomposition of the cellulose component is suppressed and its yield increases, and generation of reaction-inhibitor components downstream is suppressed.

Furthermore, since water 19 is poured into the slurrying tank 21, and the liquid 21b is present, a liquid seal is formed at the gas-liquid interface 13a of the hydrothermal decomposition section 17 and at the gas-liquid interface 21a of the slurrying tank 21, and leakage of the pressurized nitrogen 25 which is gas used for pressurizing is thereby prevented. As a result, there is no loss due to gas leaks, and running costs related to gas used for pressuring can be greatly reduced. Note that a safety valve and an inflow passage (not illustrated) of the pressurized nitrogen 25 are formed in the slurrying tank 21.

Furthermore, by slurrying the biomass solid 20, it becomes possible to fluidize the biomass solid 20, and the discharge mechanism for discharging it from the slurrying tank 21 to the outside becomes simple. Specifically, if the biomass solid 20 remains in the high-temperature state, an expensive material needs to be used in the discharge mechanism, but in this embodiment, since it is cooled in the slurrying tank 21, inexpensive stainless steel, resin, or the like can be used as the material of the discharge section 23 provided on the discharge side thereof. As the discharge section 23, for example, a rotary feeder, flow regulating valve, or the like may be used.

Furthermore, handling of the biomass solid 20 as a solid has been complex, but in this embodiment, fluidity can be improved by slurrying, and handling becomes easy.

Additionally, because saccharification and the like are enzymatic reactions, cooling to below a prescribed temperature (for example, not greater than 60° C.) is required. At this time, a large-scale heat exchange means is required because the heat exchange efficiency is poor when cooling the biomass solid 20 in that state, but by slurrying, cooling efficiency is good and a large-scale heat exchange means becomes unnecessary.

Furthermore, an indirect cooling means may be provided for cooling inside the slurrying tank 21. Additionally, a stirring means 22 is provided in the slurrying tank 21, but the present invention is not limited thereto, and stirring may be performed by, for example, a circulation means using a pump.

Here, the biomass slurry 24 obtained in the slurrying tank 21 is discharged from the discharge section 23, passes through the discharge line $L_1$, and is introduced into the settling tank 31 which settles the biomass slurry 24.

Figure 3:
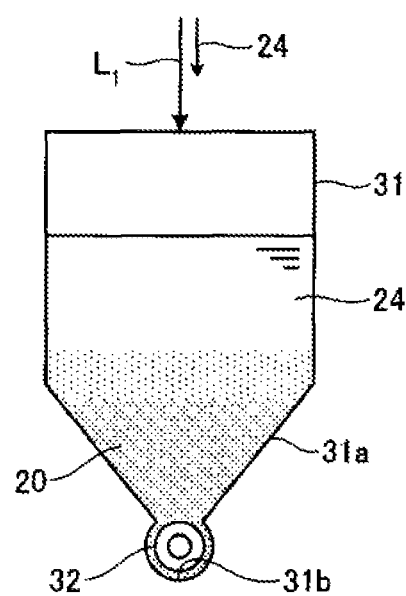
FIG. 3 is a frontal schematic view illustrating a solid-liquid separation apparatus according to embodiment 1.

This settling tank 31 has a shape that collects the sediment on the bottom 31b thereof. For example, as illustrated in FIG. 3, a tapered side wall 31a is formed below the middle portion. Using opposing tapered side walls 31a, it is easy to collect the sediment (biomass solid 20) obtained from the biomass slurry 24.

A screw means 32, driven by a drive motor $M_3$, is provided on the bottom 31b of the settling tank 31. By rotation of the screw means 32 by the drive motor $M_3$, the sediment that settled on the bottom 31b is discharged to outside the system.

On the bottom 31b of the settling tank 31, the scooping-up and conveying means 34, which has the screw conveyor 35 which separates water while scooping up the biomass solid 20, is disposed via a connecting section 33.

In this scooping-up and conveying means 34, the screw conveyor 35 provided inside is inclinedly provided, from the bottom 34a with the connecting section 33 to the top end 34b. By rotating the internal screw conveyor 35 by a drive motor $M_4$, it scoops up the biomass solid 20 from bottom to top, and while scooping, separates the contained water 19.

On the top end 34b of the scooping-up and conveying means 34, a discharge port 34c, which discharges the concentrated biomass slurry 36, is provided.

Furthermore, a water receiving tank 37 is adjacent to the settling tank 31, and water 19 that overflows from the settling tank 31 is transferred thereto by a line $L_2$.

A stirring means 37a may also be provided in the water receiving tank 37. In this case, the biomass solid 20 is partially mixed into the water 19, and in the event that the biomass solid 20 settles in the water receiving tank 37, the biomass solid 20 is homogenized by rotating the stirring means 37a using a motor $M_5$.

The water 19 in this water receiving tank 37 is cooled by a cooler 39 while being returned to the slurrying tank 21 via a return line $L_3$ by a pump 38, and the water 19 can be reused.

In the embodiment described above, the water separated by the solid-liquid separation apparatus 30 is cooled by the cooler 39 and returned in this state to the slurrying tank 21, but the present invention is not limited thereto.

As illustrated in FIG. 2, in a biomass treatment system 10B, an biological treatment apparatus 45 that biologically treats the water 19 separated by the solid-liquid separation apparatus 30, is provided in the return line $L_3$ in the biomass treatment system 10A of embodiment 1. After the biological-treated water 19 is cooled by the cooler 39, the water 19 is returned to the slurrying tank 21.

Because the water separated by the solid-liquid separation apparatus 30 contains organic acids (for example, formic acid, acetic acid, citric acid, and the like), which are reaction-inhibitor substances downstream, they are decomposed and removed by the treatment apparatus 45. Because treatment is reliably accomplished and inhibitor substances have been removed when the water 19 is reused, there is no increase in inhibitor substances when the reaction is quenched in the slurrying tank 21. Furthermore, by using, for example, a methane enzymatic biological treatment apparatus as the biological treatment apparatus 45, methane can be recovered and reused in fuel and the like.

Next, the procedure for separating water 19 from the biomass slurry 20 by the settling tank 31 and the scooping-up and conveying means 34 will be described.

Here, the settling tank 31 is at atmospheric pressure, and the biomass slurry 24 is introduced into the settling tank 31 via the line $L_1$. The biomass solid 20 in the introduced biomass slurry 24 settles naturally by its own weight onto the bottom 31b of the settling tank 31.

On the bottom 31b of the settling tank 31, the screw means 32 which discharges the sediment (biomass solid 20) is provided, and the sediment is conveyed and discharged to the bottom 34a of the scooping-up and conveying means 34 via the connecting section 33 connected on the bottom 31b of the settling tank 31.

The conveyed sediment is scooped up by the screw conveyor 35 provided inside, from the bottom 34a toward the top end 34b of the scooping-up and conveying means 34. During this scooping up, the water and the biomass solid 20 are separated and the biomass solid 20 is conveyed upward, and as a result, the concentrated biomass slurry 36 is discharged via the discharge port 34c from the top end 34b of the scooping-up and conveying means 34.

As a result, in the slurrying tank 21, the biomass solid 20 having a dilute solid concentration of, for example, 5% by weight, can be concentrated to a solid concentration of not less than 10 to 30% by weight by putting in water for slurrying thereof, so that it can have a solid concentration suitable for saccharification.

In this embodiment, a screw conveyor 35 was given as an example of the conveying means of the scooping-up and conveying means 34, but the present invention is not limited thereto, and a belt conveyor or the like may be used.

Furthermore, it may be introduced by a discharge line for blowing $L_{11}$ provided for discharging biomass accumulated over a long period and discharging the contents of maintenance resin from the bottom 34a of the scooping-up and conveying means 34. Additionally, water for cleaning 42 may be introduced by an introduction line $L_{12}$ from the top end 34b of the scooping-up and conveying means 34, so as to enable cleaning of the interior periodically or when clogging occurs.

Here, in the embodiment described above, the scooping-up and conveying means 34 having the screw conveyor 35 which separates water while scooping up the biomass solid 20 via the connecting section 33 was provided at the bottom 31b of the settling tank 31, but the present invention is not limited thereto.

Figure 4:
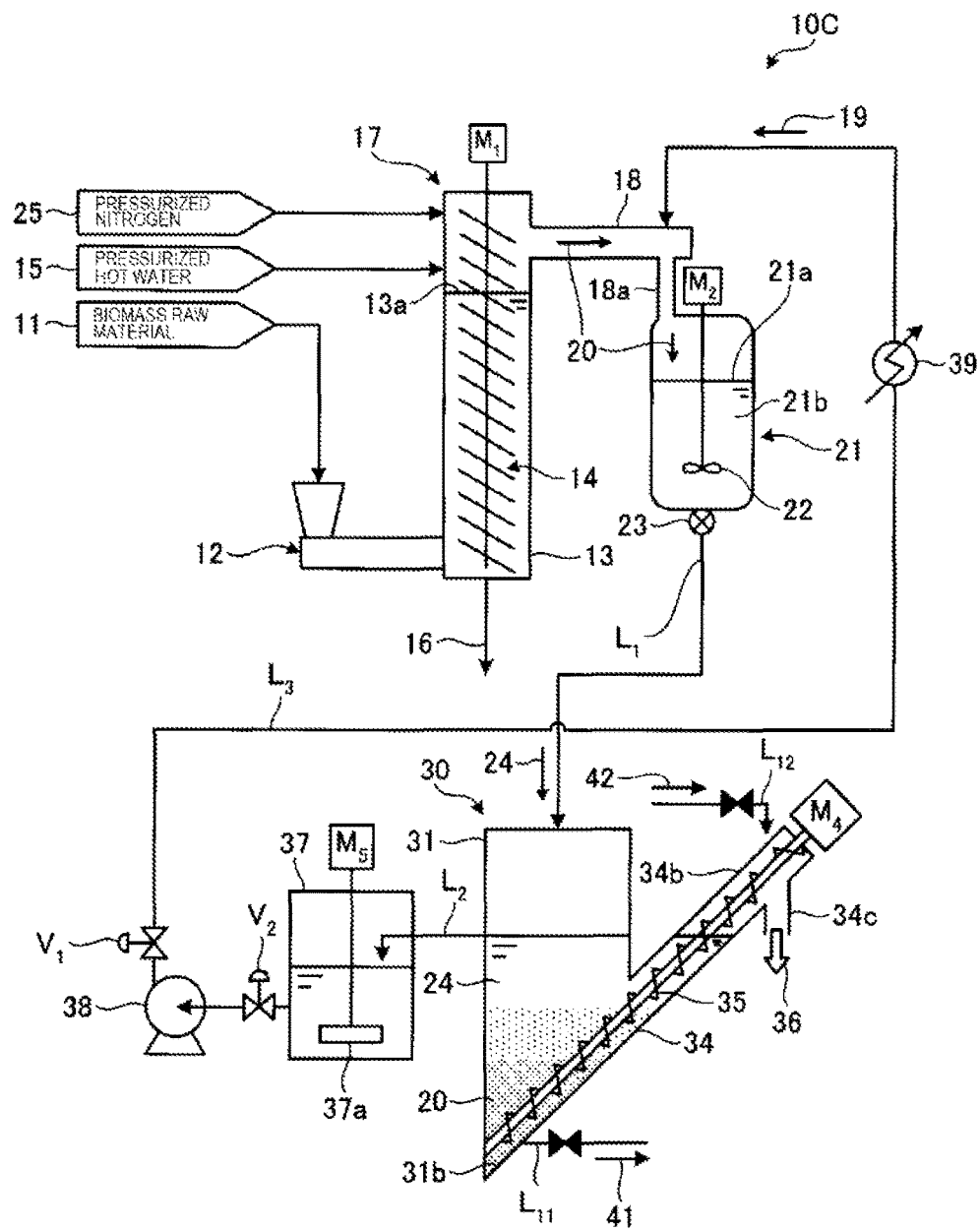
FIG. 4 is a schematic view illustrating another biomass treatment system according to embodiment 1.

FIG. 4 is a schematic view illustrating another biomass treatment system according to this embodiment.

As illustrated in FIG. 4, in a biomass treatment system 10C according to this embodiment, the scooping-up and conveying means 34 is integrally provided on the lower section of the settling tank 30.

Specifically, the bottom 31b of the settling tank 31 is inclined, and the scooping-up and conveying means 34 is integrally provided along that inclination, and the settled biomass solid 20 is scooped up as-is by the screw conveyor 35. By so doing, the screw means 32 and the connecting section 33 are unnecessary, and the apparatus can be simplified.

Here, the biomass supplied to the hydrothermal decomposition section 17 refers to accumulation of organisms or organic matter derived from organisms incorporated in the substance circulation system of the global biosphere (see JIS K 3600 1258) without particular limitation, but in the present invention, the use of wood biomass such as broad-leaf trees, cellulose-based resources such as herbaceous biomass, agricultural waste, food waste, and the like is particularly preferred.

Furthermore, the biomass raw material 11 is not particularly limited in particle size, but it is preferably pulverized to not greater than 5 mm.

In this embodiment, the biomass may also be pretreated using, for example, a pulverizing apparatus as a raw material adjustment apparatus before supplying the biomass. Furthermore, it may also be cleaned by a cleaning apparatus.

Note that when hull or the like is used as the biomass raw material 11, it may be supplied to the biomass supply section 12 as-is without being pulverized.

Furthermore, the reaction temperature in the hydrothermal decomposition section 17 is preferably in the range of 180° C. to 240° C. It is more preferably from 200° C. to 230° C.

This is because at low temperatures below 180° C., the hydrothermal decomposition rate is low and a long decomposition time is required, leading to an increase in size of the apparatus, which is undesirable. On the other hand, at temperatures exceeding 240° C., the decomposition rate becomes excessively high, and transfer of the cellulose component from a solid to a liquid side increases and excessive decomposition of hemicellulose-based saccharides is promoted, which is undesirable.

Additionally, the hemicellulose component starts to decompose at approximately 140° C., cellulose at approximately 230° C., and the lignin component at approximately 140° C., but the range of 180° C. to 240° C. is preferred because cellulose remains on the solid side while the hemi-cellulose component and lignin component have sufficient decomposition rates.

The reaction pressure is preferably a pressure in which pressure from 0.1 to 0.5 MPa is further added to the saturated vapor pressure of water at each reaction temperature (from 180° C. to 240° C.) of the main section 13.

The reaction time is not greater than 20 minutes, and preferably from 3 to 10 minutes. This is because if the reaction is carried out for a long time, the proportion of excessive decomposed matter increases, which is undesirable.

Examples of the biomass supply section 12 which supplies the biomass from atmospheric pressure to increased pressure include means such as a screw, a piston pump, a slurry pump, and the like.

Furthermore, the hydrothermal decomposition section 17 of the hydrothermal decomposition apparatus is installed vertically in this embodiment, but the present invention is not limited thereto, and an inclined hydrothermal decomposition apparatus having a gas-liquid interface 13a may be used.

Here, an inclined or vertical hydrothermal decomposition apparatus is preferable because gas generated in the hydrothermal decomposition reaction and gas carried into the raw material and the like can be quickly discharged from above. Furthermore, since the decomposition products are extracted by the pressurized hot water 15, the concentration of extracted products increases from the top toward the bottom, which is preferable from the perspective of extraction efficiency.

As described above, according to this embodiment, the cellulose main component and the hemicellulose component are decomposed from the biomass raw material in a state of solid-liquid contact, and then, by putting the biomass solid, which is the decomposition product thereof, into the liquid 21b that was poured into the slurrying tank 21, resulting in slurrying the biomass solid and forming a liquid seal, and preventing leakage of pressurized gas. As a result, leakage of gas used for pressurizing (for example, pressurized nitrogen or the like) can be prevented, and running costs can be greatly reduced.

Then, in the biomass slurry 24 that was slurried in the slurrying tank 21, the biomass solid 20 is settled by the settling tank 31, and then the water content thereof is separated by the scooping-up and conveying means 34 having the screw conveyor 35, which separates the water content while scooping up the sediment, and the concentrated biomass slurry 36 can be obtained.

As a result, it is unnecessary to provide an expensive dehydration means such as a filter press means or centrifugal separation means. Furthermore, since dehydration means such as filter press means and centrifugal separation means run intermittently, they are unsuitable for continuous treatment, and therefore, the saccharifying fermentation and purification processes downstream cannot be improved in efficiency. The filter press means and centrifugal separation means also increase running costs because they require power and a large amount of water for settling the biomass slurry 24.

In contrast, with the solid-liquid separation apparatus 30 of the present invention, solid-liquid separation can be performed continuously and at a low running cost, and the fermentation and purification processes can be improved in efficiency.

From the above facts, according to this embodiment, by separating water 19 which contains reaction-inhibitor substances from the biomass slurry 24 in the solid-liquid separation apparatus 30, it is possible to efficiently remove reaction-inhibitor substances, and the reactions downstream are well.

Embodiment 2

Next, another embodiment of the biomass treatment system according to the present invention will be described in reference to the drawings. Note that members that are the same as the biomass treatment system of embodiment 1 are given the same reference numerals, and descriptions thereof are omitted.

Figure 5:
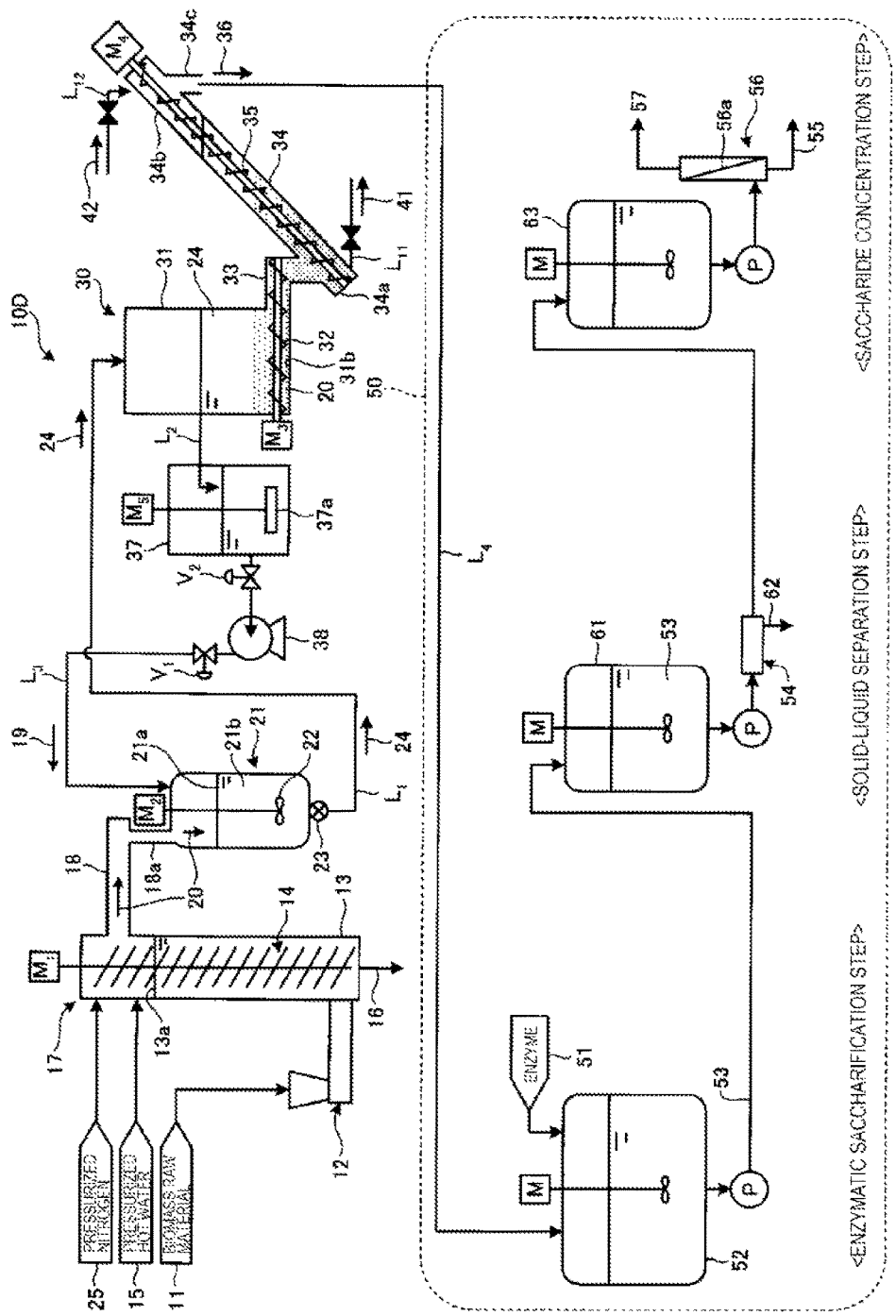
FIG. 5 is a schematic view illustrating a biomass treatment system according to embodiment 2.
Figure 6:
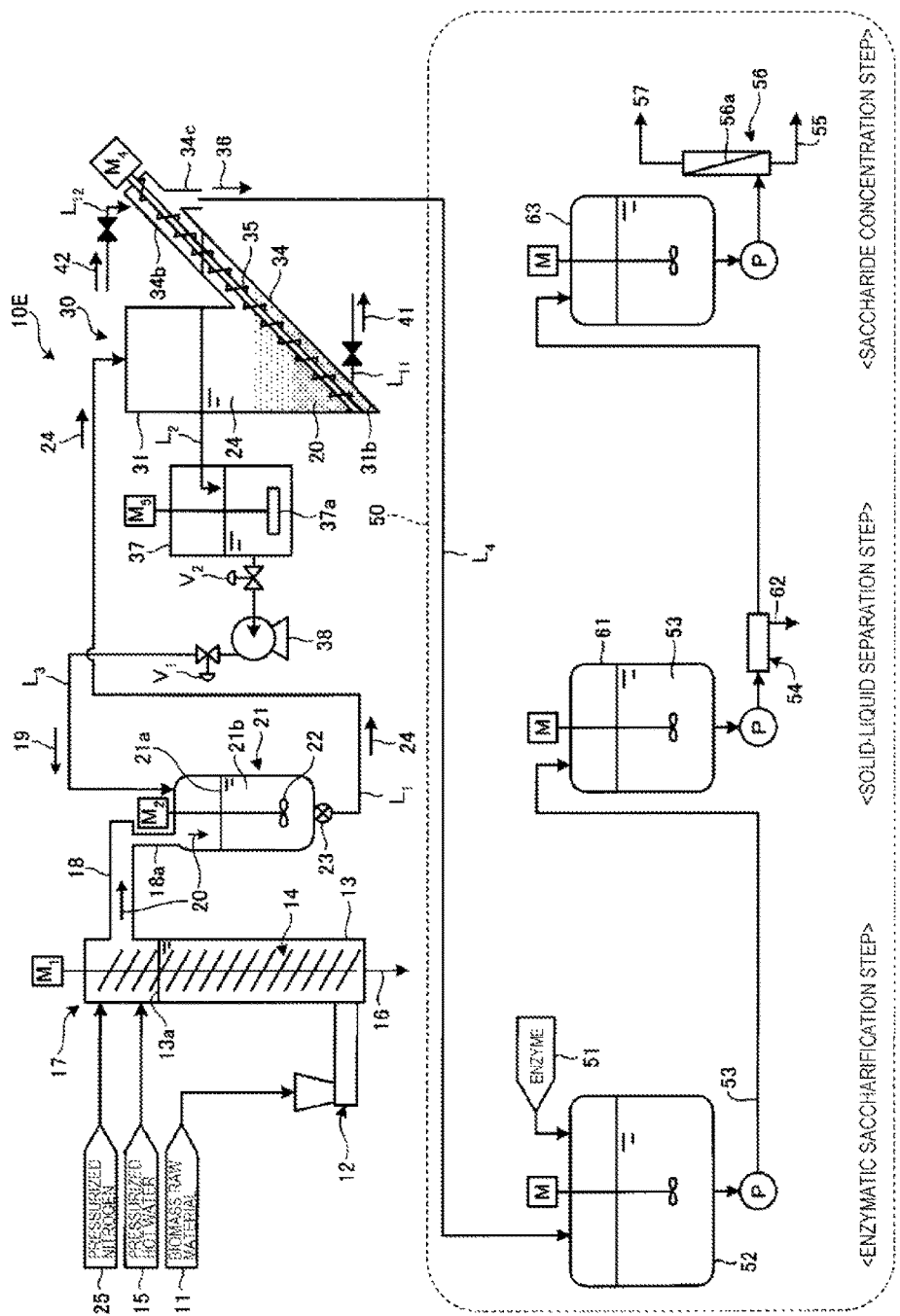
FIG. 6 is a schematic view illustrating another biomass treatment system according to embodiment 2.

FIG. 5 is a schematic view illustrating a biomass treatment system according to embodiment 2. FIG. 6 is a schematic view illustrating another biomass treatment system according to embodiment 2.

As illustrated in FIG. 5, a biomass treatment system 10D is the biomass treatment system 10A of embodiment 1 having a solid-liquid separation apparatus (separated type), further comprising a C6 saccharification/saccharide concentration apparatus 50, which enzymatically saccharifies biomass solid containing primarily a cellulose component to a six-carbon saccharide (C6 saccharide), and concentrates the saccharide. As illustrated in FIG. 6, a biomass treatment system 10E is the biomass treatment system 10A of embodiment 1 having another solid-liquid separation apparatus (integrated type), further comprising a C6 saccharification/saccharide concentration apparatus 50, which enzymatically saccharifies biomass solid containing primarily a cellulose component to a six-carbon saccharide (C6 saccharide), and concentrates the saccharide. Note that the saccharification method is described below using FIG. 5, as the operations are the same in both.

This C6 saccharification/saccharide concentration apparatus 50 has a water content separation apparatus 56 comprising a saccharification tank 52, which uses an enzyme 51 to enzymatically saccharify the concentrated biomass slurry 36 that was concentrated in the solid-liquid separation apparatus 30; a saccharide solution solid-liquid separation apparatus 54, which separates the solid from a saccharide solution 53 after saccharification; and a reverse osmosis (RO) membrane 56a, which removes water 57 from the saccharide solution 53 separated in the saccharide solution solid-liquid separation apparatus 54, to obtain a concentrated saccharide solution 55.

As the saccharide solution solid-liquid separation apparatus 54, for example, a screw decanter, sand filtration apparatus, MF membrane or the like may be used alone or in combination, so that it can protect the reverse osmosis (RO) membrane 56a while removing the solids. Additionally, by using an ultrafiltration (UF) membrane before the RO membrane 56a, the RO membrane 56a can be protected and the enzyme can be recovered and reused.

Furthermore, a loose RO membrane, nanofiltration (NF) membrane, or the like may also be used in the water content separation apparatus 56.

Next, the procedure of the treatment steps of the C6 saccharification saccharide concentration apparatus 50 will be described.

<Enzymatic Saccharification Step>

First, in the saccharification tank 52, the concentrated biomass slurry 36 is introduced via a supply line $L_4$, the enzyme 51 is added, and saccharification takes place by an enzymatic reaction in the enzymatic saccharification step.

<Solid-Liquid Separation Step>

Then, the saccharide solution 53 is accumulated in a saccharide solution tank 61, and after that, a solid residue solution 62 of lignin and the like is separated by the saccharide solution solid-liquid separation apparatus 54, and then the saccharide solution 53 is accumulated in a saccharide solution tank 63.

<Saccharide Concentration Step>

Then, the water 57 is removed from the saccharide solution 53 by the water content separation apparatus 56 having the RO membrane 56a, and the concentrated saccharide solution 55 is obtained.

This concentrated saccharide solution 55 serves as the various organic raw materials in the fermentation of later steps (not illustrated).

In the present embodiment, the saccharide can be concentrated efficiently by membrane treatment using various membranes.

Furthermore, the separated solid residue solution 62 of lignin or the like can be used for fuel because it has a high calorific value. The solid residue solution 62 of lignin or the like can also be used for organic fertilizer or chemical raw materials (use as a lignin adhesive or the like).

In this way, in the saccharide solution producing method using biomass raw material of the present invention, as illustrated in FIG. 5, a biomass raw material 11 having cellulose, hemicellulose, and lignin is supplied from atmospheric pressure to increased pressure, and this biomass raw material 11 is hydrothermally decomposed by the hydrothermal decomposition section 17 using pressurized hot water 15, and the lignin component and hemicellulose component are dissolved in the pressurized hot water 15, and after that, the biomass solid 20 discharged from the hydrothermal decomposition section 17 is put into a slurrying tank 21, which is connected to the hydrothermal decomposition section 17 and into which water is poured, and formed into a biomass slurry 24, and the biomass slurry 24 is enzymatically saccharified to produce a saccharide solution 53, after which the solid is separated, and water is removed. By this process, a saccharide solution 53 can be efficiently produced from a biomass raw material 11.

Using the saccharide solution obtained by this saccharide solution producing method using biomass raw materials, alcohol fermentation of methanol, ethanol, or the like can be performed, and alcohol can be produced.

Additionally, by forming the biomass solid matter into slurry, the biomass solid matter is easy to handle and is suitable for a subsequent saccharification step, and a saccharide solution (C6 saccharide) can be efficiently produced. Furthermore, with this saccharide solution as a starting point, various organic raw materials (for example, alcohols, petroleum substitutes, amino acids, or the like) can be efficiently produced. Additionally, with this saccharide solution as a starting point, various organic raw materials (for example, alcohols, petroleum substitutes, amino acids, or the like) of LPG, automobile fuel, aircraft jet fuel, kerosene, diesel oil, various heavy oils, fuel gas, naphtha, ethylene glycol which is a decomposition product of naphtha, lactic acid, alcohols (ethanol and the like), amines, alcohol ethoxylates, vinyl chloride polymers, alkyl aluminum, PVA, vinyl acetate emulsions, polystyrene, polyethylene, polypropylene, polycarbonate, MMA resin, nylon, polyester, and the like can be efficiently produced. Thus, biomass-derived saccharide solutions can be efficiently utilized as substitutes for chemical products derived from crude oil, which is a depleted resource, and raw materials for producing those substitutes.

Additionally, since the biomass solid is put into a liquid, the reaction can be efficiently quenched by cooling the biomass solid by direct heat exchange using the liquid, and furthermore, excessive decomposition of the residual hemicellulose, residual lignin, and the main component cellulose that accompanies the biomass solid is suppressed because the acid or alkali is diluted. As a result, generation of reaction-inhibitor components can be suppressed and recovery of the cellulose component can be improved.

In the present invention, when obtaining the biomass slurry, the biomass slurry is settled in a settling tank, and the settled biomass solid undergoes solid-liquid separation by a scooping-up and conveying means, for example, a screw conveyor, thereby removing water and making it into a concentrated biomass slurry. Furthermore, it is possible to remove water as well as reduce the content of reaction-inhibitor substances in cases where the biomass slurry contains reaction-inhibitor substances, thereby obtaining the concentrated biomass solid having high purity.

REFERENCE SIGNS LIST 10A to 10E Biomass treatment systems
11 Biomass raw material
12 Biomass supply section
13 Main section
14 First screw means
15 Pressurized hot water
16 Hot water discharge liquid
17 Hydrothermal decomposition section
18 Biomass solid discharge section
19 Water
20 Biomass solid
21 Slurrying tank
22 Stirring means
23 Discharge section
24 Biomass slurry
25 Pressurized nitrogen
30 Solid-liquid separation apparatus
31 Settling tank
34 Scooping-up and conveying means
36 Concentrated biomass slurry

The invention claimed is:

1. A biomass treatment system comprising:
a biomass treatment section comprising a treatment column having a gas-liquid interface configured to decompose a biomass raw material containing cellulose, hemicellulose, and lignin under high-temperature, and high-pressure conditions, and thus removing a lignin component and a hemicellulose component from the biomass;
a biomass solid discharge section configured to discharge a biomass solid treated by the biomass treatment section;
a slurrying tank that is connected to the biomass solid discharge section, the slurrying tank configured to pour water into the biomass solid discharge section and to slurry the discharged biomass solid;
a solid-liquid separation apparatus including a settling tank configured to settle the biomass solid, the settling tank being provided downstream of the slurrying tank, and a screw conveyor or a belt conveyor, a bottom of which is disposed on a lower side of a bottom of the settling tank and is connected thereto via a connecting section and is inclinedly provided from a bottom to a top end thereof, and which is configured to scoop up a biomass sediment conveyed from the bottom of the settling tank from the bottom of the screw conveyor or the belt conveyor toward a top end thereof and separate water and discharge a thus obtained concentrated biomass slurry from the top end thereof via a discharge port;
a water receiving tank configured to receive water overflown from the settling tank;
a line connected between the settling tank and the water receiving tank and configured to transfer the water overflow from the settling tank to the water receiving tank; and
a return line that is connected between the water receiving tank and the slurrying tank and is configured to return the water from the water receiving tank to the slurrying tank;
wherein the screw conveyor or the belt conveyor includes a blowing line provided on the bottom thereof, the blowing line configured to discharge biomass accumulated outside of the system to prevent from clogging.

2. The biomass treatment system according to claim 1, further comprising
a saccharification tank configured to saccharify the concentrated biomass slurry separated by the solid-liquid separation apparatus.

3. The biomass treatment system according to claim 1, wherein
the biomass treatment section is any one of a hydrothermal decomposition section, an alkali decomposition section, or an acid decomposition section.

4. The biomass treatment system according to claim 1, wherein the screw conveyor or the belt conveyor includes an introduction line provided at a top end of the screw conveyor or the belt conveyor, the introduction line configured to introduce cleaning water into an interior thereof.

* * * * *